(12) United States Patent
Tidwell

(10) Patent No.: US 7,228,579 B2
(45) Date of Patent: Jun. 12, 2007

(54) PORTABLE PATIENT SUPPORT DEVICE AND METHOD OF PREPARING PATIENT FOR PROSTATE BRACHYTHERAPY

(76) Inventor: Thomas J. Tidwell, 2121B Warm Springs Rd., Columbus, GA (US) 31904

( * ) Notice: Subject to any disclaimer, the term of this patent is extended or adjusted under 35 U.S.C. 154(b) by 110 days.

(21) Appl. No.: 11/052,490

(22) Filed: Feb. 4, 2005

(65) Prior Publication Data

US 2005/0166325 A1    Aug. 4, 2005

Related U.S. Application Data

(60) Provisional application No. 60/542,064, filed on Feb. 4, 2004.

(51) Int. Cl.
*A61G 1/00* (2006.01)
*A61B 6/04* (2006.01)
(52) U.S. Cl. .................. 5/624; 5/648; 5/81.1 HS; 5/626; 378/209
(58) Field of Classification Search ............ 5/624–626, 5/648, 81.1 R, 81.1 C, 81.1 HS
See application file for complete search history.

(56) References Cited

U.S. PATENT DOCUMENTS

| | | | |
|---|---|---|---|
| 2,978,713 A * | 4/1961 | Scalzitti et al. ................ | 5/648 |
| 4,686,719 A | 8/1987 | Johnson et al. ............... | 5/81 R |
| 5,067,189 A | 11/1991 | Weedling et al. ............. | 5/81 R |
| RE35,299 E | 7/1996 | Weedling et al. ........... | 5/81.1 T |
| 5,561,873 A | 10/1996 | Weedling ...................... | 5/711 |
| 5,871,220 A * | 2/1999 | Lombard .................... | 280/79.7 |
| 6,073,291 A | 6/2000 | Davis ............................ | 5/711 |
| 6,138,306 A | 10/2000 | Muhanna ...................... | 5/706 |
| 6,484,332 B2 * | 11/2002 | Korver et al. ............. | 5/81.1 R |
| 6,701,544 B2 * | 3/2004 | Heimbrock ................ | 5/81.1 R |
| 2002/0166168 A1 | 11/2002 | Weedling et al. .......... | 5/81.1 R |

* cited by examiner

Primary Examiner—Michael Trettel
(74) Attorney, Agent, or Firm—Drinker Biddle & Reath LLP

(57) ABSTRACT

A portable patient support includes a platform having a rigid platform received in an interior of an end cap. Elongated rails attached to side walls of the end cap receive accessories, such as stirrups for elevating a patient's legs during insertion of brachytherapy needles for treating prostate cancer and a leg support table for comfortable support of a patient's legs during transport. The portable patient support also has a transfer device including an inflatable mattress having micro-fenestrations in a bottom sheet or a semi-rigid sliding member located beneath the platform. The platform is preferably secured to the transfer device, using straps or by receipt of the platform in built-in pocket. Alternatively, the support may include a fenestrated lower tray attached to the platform by expandable connectors to contain the transfer device. A method of preparing a patient for prostate brachytherapy using the portable patient support is described.

17 Claims, 5 Drawing Sheets

PORTABLE PATIENT SUPPORT DEVICE AND METHOD OF PREPARING PATIENT FOR PROSTATE BRACHYTHERAPY

CROSS REFERENCE TO RELATED APPLICATIONS

The present application claims priority from U.S. Provisional Application No. 60/542,064, filed Feb. 4, 2004, which is incorporated herein in its entirety.

FIELD OF THE INVENTION

The present invention relates to the field of portable platforms for supporting patients during medical procedures, and to the field of brachytherapy for the treatment of prostate cancer.

BACKGROUND OF THE INVENTION

Prostate cancer patients can be treated using a procedure known as brachytherapy. In a brachytherapy prostate procedure, tiny pellets or "seeds" of a highly radioactive material such as Palladium 103, Iodine 125, or Iridium 192 are implanted directly into or adjacent to the cancer tumor using needles. The radiation may be delivered by permanent low dose rate seeds placed through open-ended interstitial needles. Alternatively, radiation may be delivered by temporary high dose rate (HDR) seeds using closed-ended needles, a procedure that does not leave the patient radioactive. The radiation from the seeds is absorbed within a small area (the Greek term "brachy" means short distance), and therefore destroys cancer cells in the prostate without adversely affecting large areas surrounding the tumor. In certain cases, this radiation delivery method is preferable to treatment using external beam radiation in which the radiation is not localized and can result in damage to healthy tissue and limited radiation delivered to the tumor.

In the general steps of performing HDR brachytherapy, the thin needles are first placed in or around the tumor. The needles are then connected to a device called an HDR afterloader, which is a computer-controlled machine that protectively houses a single high intensity radioactive seed source. The afterloader inserts the seed source on the end of a wire through a transfer tube and into the closed-ended needle. The wire is then paused at multiple dwell positions to apply dosage in accordance with a dosage plan. The radioactive seed source is then withdrawn by the wire to the protective housing of the afterloader. This procedure is then repeated for some, or all, of the remaining delivery needles depending on the dosage plan.

There is a complicating factor in HDR brachytherapy for prostate cancer. The insertion of the brachytherapy needles is done with the patient lying on his back on a procedure table or hospital bed with his legs elevated in stirrups. Following needle placement, the patient is moved to a different room, sometimes even a different medical facility, where a CT scanner is used for imaging the tumor and needles to create a computerized dosage template for delivery of the radioactive seeds. The patient is then moved from the CT scanner to yet another location with an HDR afterloader for delivery of the radiation dose based on the computerized template. The movement of the patient during the entire procedure may require transfer from the procedure table for the needle insertion to a gurney and/or ambulance for transport to the CT scanner, transfer to a radiolucent platform for the CT imaging, and then further transfers from the radiolucent platform to a gurney and/or ambulance to the HDR facility and to the treatment platform for the dosage delivery.

This repeated transfer and transport of the patient may cause displacement or even dislodgement of the needles, resulting in uncertainty regarding the proper positioning of the needles when they are presented to the HDR afterloader. Since the computerized dosimetric plan was based upon the needle placement as imaged at the CT scanner to deliver precision dosage to specific locations, any movement of an interstitial treatment needle between the CT imaging and the radioactive seed insertion will degrade the level of precision.

Despite this need to keep the needle placement constant, it is normal practice to place a patient's legs in a lowered position as he lies on his back for transfer and transport. This too often causes the inserted needles to be pulled downwardly by folds of tissue in the pelvic area or to be moved by contact with the mattress on the gurney or ambulance stretcher. Such needle movement increases the uncertainty regarding needle positioning. Such needle movement can also be uncomfortable for the patient and can possibly lead to relatively serious injury.

In recognition of these problems, I have developed a portable patient support device, as described below. Although the device is configured for effective use in preparing a patient for prostate HDR brachytherapy, and its use described in relation to that procedure, it should be noted that the device can be configured for other procedures, either other radiotherapy procedures such as radioactive material implantation of the cervix and uterus or for immobilization and transportation of neurosurgery or orthopedic surgery patients.

SUMMARY OF THE INVENTION

A portable patient support device is presented with features of an operating room table which is light weight enough to allow it and the patient to be transported by its own handles. This device also can be used with and without an additional transfer mechanism such as an inflatable transfer mattress having an air plenum with a pattern of tiny escape holes (micro-fenestrations) in its bottom sheet to create a cushion of air to facilitate sliding movement of the mattress. An air mattress shown in the pilot models is the currently commercially available air plenum transfer mattress known as the AirPAL transfer pad sold by Patient Transfer Systems, Inc. My new immobilization and transport device includes a relatively rigid platform, such as a plastic hospital stretcher, optionally secured on top of an inflatable plenum transfer mattress or other sliding device by straps or other fasteners, or by the insertion of the inflatable plenum chamber into a pocket inherently connected to the bottom of the platform. Optionally an inflatable transfer air plenum mattress can be constructed with a pocket on its top side to receive and hold the rigid stretcher. The device further includes a structurally rigid hollow base (or end cap) having top, bottom and side walls for receiving one end of the platform. A pair of rails, preferably matching the profile of typical hospital operating table side rails, are located on opposite sides of the end cap and are supported from the side walls of the end cap by stand-offs at a distance sufficient to mount stirrups or other operating room medical accessories.

The portable patient support device is particularly suited for preparing a patient during a brachytherapy procedure for treating prostate cancer. A rigid plastic stretcher and end cap device are assembled securely together as a unit that is then either strapped onto an inflatable transfer mattress or received into a pocket in the top surface of the mattress. The thus connected device is placed on a preparation table or hospital bed with the transfer mattress deflated.

The patient is then laid on his back on the stretcher. A height-adjustable leg support stirrup is placed on each of the rails. The patient's legs are then raised in the stirrups to place the patient into position for the HDR needles to be inserted in or around the prostate gland.

After the needles are placed, the stirrups are removed from the rails and are replaced by a leg support table The table has channels that are slidably received and secured on the rails. The table's top side is a platform adapted to support the patient's legs above the stretcher at a height that may be less than that at which the legs were supported in the stirrups, but still sufficient to keep the needles and attached HDR transfer tubes from sagging or contacting the plartform. The patient can be transferred and transported on the device in this leg-raised position through the brachytherapy procedure.

The patient and portable support device are moved together. Since the patient cannot be rolled or sit up to be moved onto a gurney or other transport, the air transfer pad or other sliding device, such as a sliding board, is used. With a gurney can be placed alongside the hospital bed, the air blower of the transfer mattress is activated to fill the plenum and create a weight-bearing cushion of air for "air-gliding" transfer of the patient support device to the gurney. Alternatively, a sliding board could be inserted between the hospital bed or couch and the patient support device and the patient support device then transferred to the gurney by sliding it over the sliding board. The same procedures can be used to transfer the patient and device from the gurney to an ambulance stretcher.

Following transport of the patient to a location having a CT scanner, the air transfer mattress can be used to air-glide the patient to a proper position under CT scanner. After the computerized dosage template is generated for the HDR afterloader to use in delivery of radioactive seeds, the transfer mattress can be used to transfer the patient back onto a gurney or ambulance stretcher for transport to the HDR treatment room. The patient's legs remain supported in the leg-raised position by the table attached to the rails, thus keeping the needles from being displaced or dislodged.

BRIEF DESCRIPTION OF THE DRAWINGS

For the purpose of illustrating the invention, the drawings depict one or more embodiment that is presently preferred. This invention is not, however, limited to the embodiment or use of the invention that is depicted in the drawings.

DETAILED DESCRIPTION OF THE DRAWINGS

Figure 1:
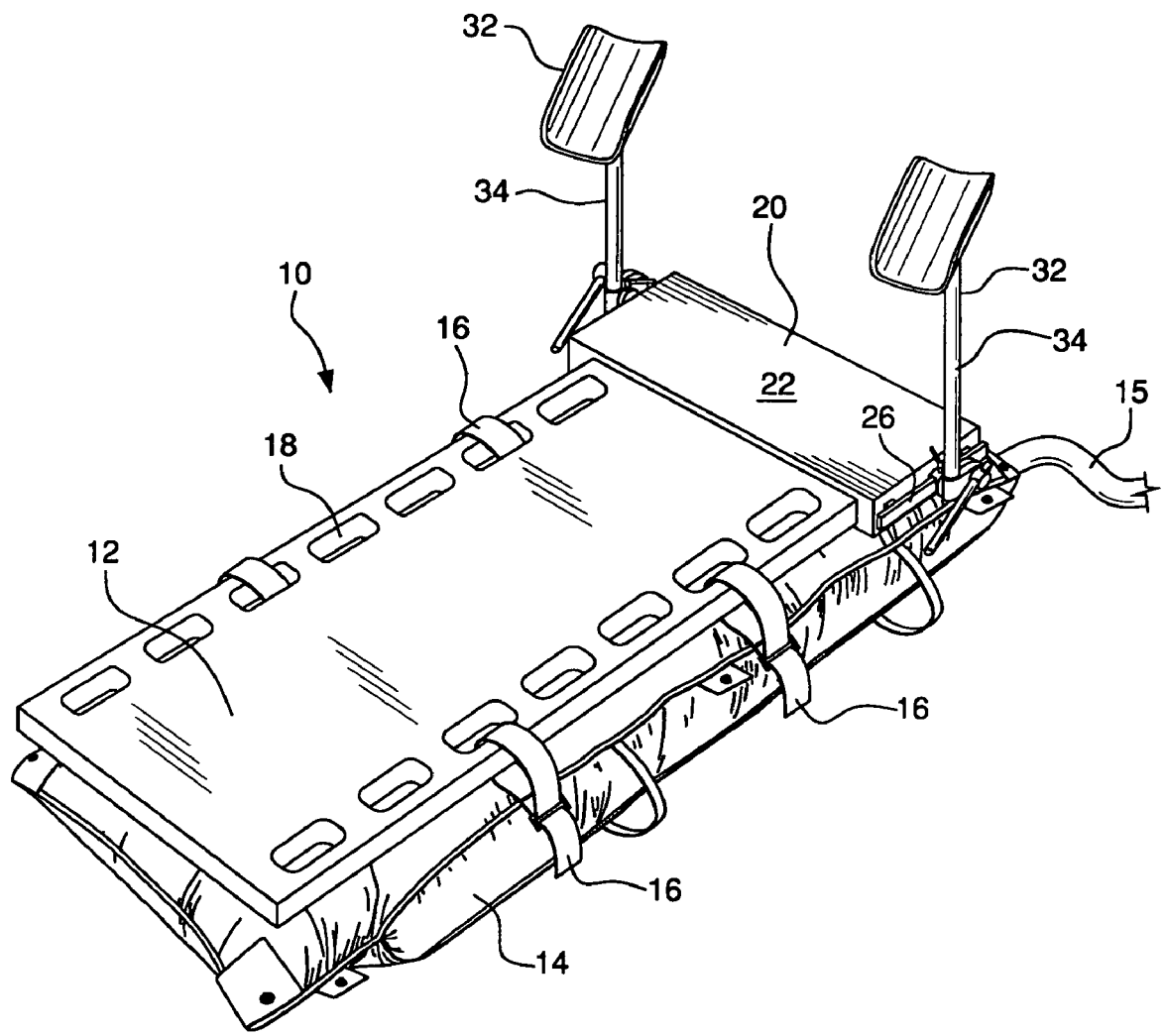
FIG. 1 is a perspective view of a portable patient support device according to the invention including a stretcher, an end cap and an inflatable transfer mattress shown in an inflated condition, the device shown with a pair of adjustable stirrups removably attached to rails on opposite sides of the end cap.

Referring to the images, where like numerals identify like elements, there is shown in FIGS. 1 through 4, a portable patient support 10 according to the present invention. As described below in greater detail, the portable patient support 10 is particularly suited for brachytherapy procedures performed on prostate cancer patients to provide necessary movement of the patient during various stages of the procedure while limiting undesirable repositioning or removal of seed-delivery needles that are inserted into the prostate. It may also be used for other medical procedures.

The portable patient support 10 includes a platform 12, in this embodiment a stretcher made from a substantially rigid material such as plastic. The portable patient support 10 also includes a patient transfer device 14, in this embodiment an inflatable transfer mattress secured to the stretcher 12 by straps 16 engaging both sides of the stretcher 12. The transfer mattress 14 includes a top sheet and a bottom sheet to form an air plenum that is inflatable by a source of pressurized air via inlet tube 15. The bottom sheet of the transfer mattress 14 includes a pattern of small holes for discharging air to create an air cushion underneath the transfer mattress 14 to facilitate horizontal sliding movement. The transfer mattress 14 is shown in the figures in an inflated condition. It should be understood that the air mattress 14 will collapse to a deflated condition when air ceases to be supplied to the air plenum from the pressurized air source.

The stretcher 12 in this embodiment includes a plurality of elongated openings 18 along its opposite sides for receiving the straps 16. As shown, the straps 16 are formed into a looped condition through the openings 18 and are received through buckles 19 to maintain the straps in the looped configuration. Any suitable method of securing the straps could be used instead of buckles. The use of buckles 19, however, allows for greater variation in the size of the loop. The portable patient support 10 is shown with four straps 16 securing the stretcher 12 to the transfer mattress 14. It should be understood, however, that a different number and placement of straps could be used, such as one or more straps enwrapping the transfer mattress 14. Both the stretcher 12 and the transfer mattress 14 are preferably radiolucent to provide for insertion under a scanning device for CT or x-ray scanning of a patient supported thereon.

Figure 4:
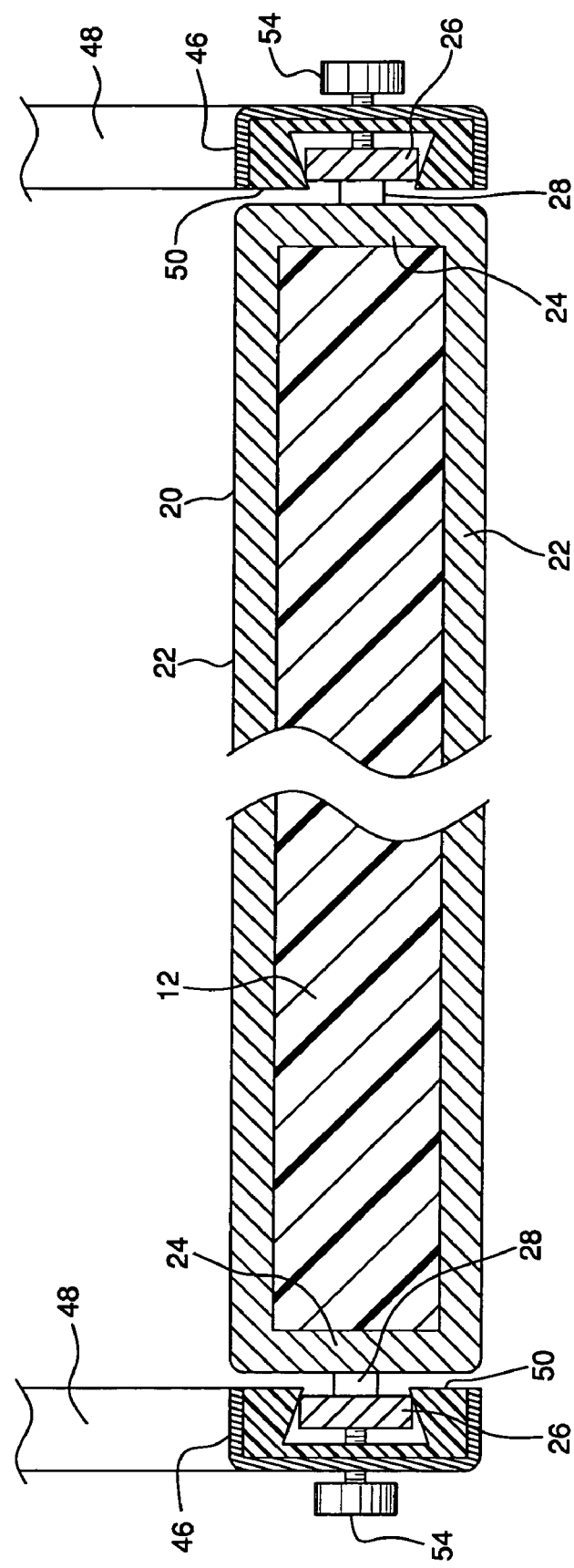
FIG. 4 is a sectional view of the end cap and stretcher of FIG. 3.

The portable patient support 10 also has an accessory support device 20, in this embodiment an end cap which includes top and bottom walls 22 and opposite side walls 24 forming a hollow box-like cavity in which an end portion of the stretcher 12 is received. The portable patient support 10 includes a pair of elongated rails 26 located on opposite sides of the end cap 20 adjacent the side walls 24. Each rail 26 is secured to stand-offs 28 formed on the side walls 24, preferably by fastening the rail to the stand-off. As shown in FIG. 4, the hollow interior cavity of the end cap 20 is preferably sized for close-fit between the stretcher 12 and the end cap 20 such that the end cap 20 is frictionally retained on the stretcher. The end cap 20 may also be secured to the support 10 by straps (not shown) from the mattress 14 looped around the stand-offs 28.

Figure 2:
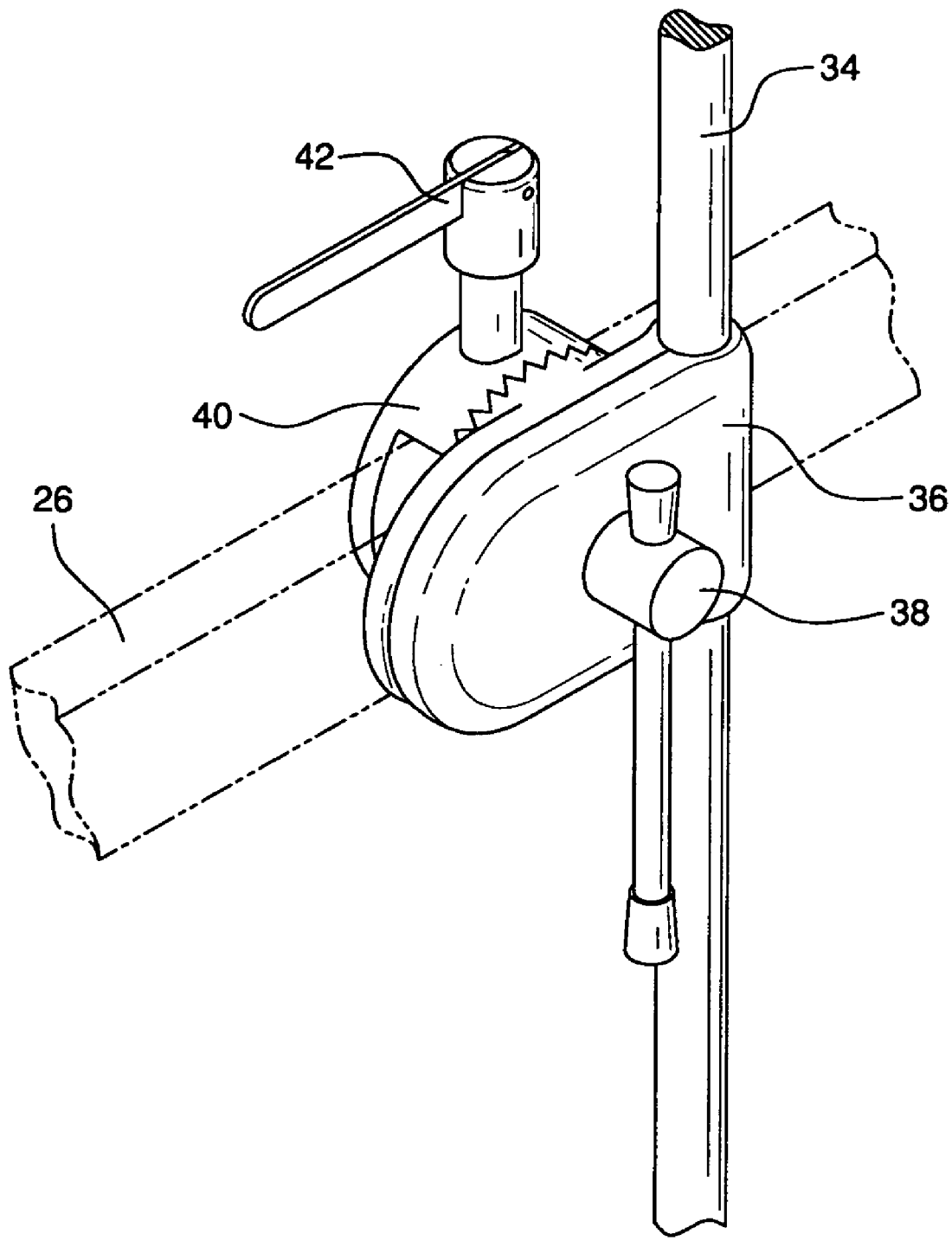
FIG. 2 is a perspective view of the equipment support mechanism of the portable patient support device of FIG. 1.

The rails 26 are preferably standard-sized operating room bed rails that may be used for supporting a variety of devices. The portable patient support 10 is shown in FIG. 1 with adjustable stirrups 32 attached to the rails 26. Referring to FIG. 2, each stirrup 32 includes an elongated post 34 slidably received by a post holder 36 and secured thereto by a clamp 38. The clamp 38 provides for adjustment of the stirrup post 34 with respect to the post holder 36. The post holder 36 also includes a rail-engaging portion 40 that is slidably received by one of the rails 26 and is secured in position thereon by a threaded stop 42. The slidable receipt of the rail-engaging portion 40 by the rail 26 provides for adjustment in the location of the stirrup 32 with respect to the transfer mattress 14.

To begin a brachytherapy procedure, a patient is placed on the portable support 10 with his back on the stretcher 12 and his feet received by the stirrups 32 in a highly elevated position with respect to the stretcher 12 to facilitate insertion of the brachytherapy needles. During this stage of the procedure, the transfer mattress 14 is preferably in its deflated condition for optimal stability of the patient.

Figure 3:
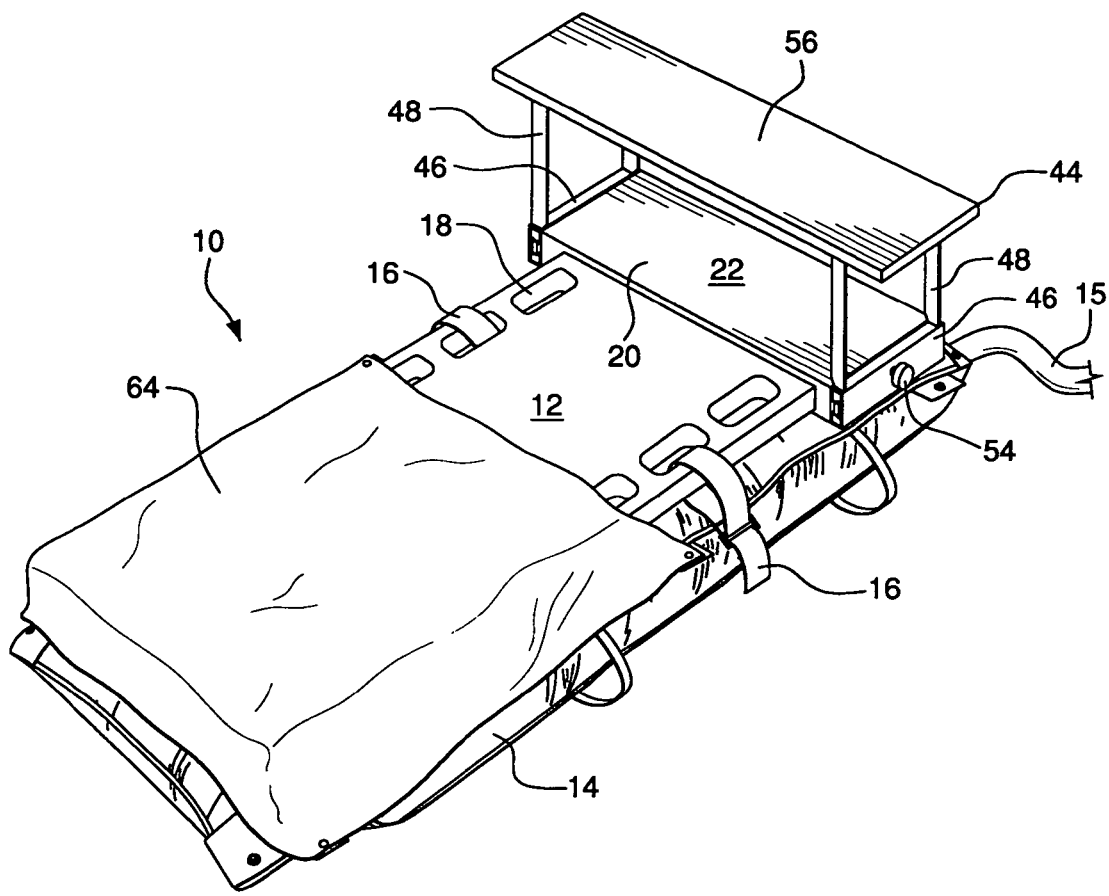
FIG. 3 is a perspective view of the portable patient support device of FIG. 1, the device shown with a leg support table removably attached to the side rails of the end cap.

Following insertion of the needles, the stirrups 32 are removed from the rails 26 and are replaced by a leg support table 44, which is shown in FIGS. 3 and 4. The leg support table 44 includes a pair of channels 46 each secured to upstanding legs 48 at opposite sides of the table 44. An insert 50 is received within each of the channels 46 and is preferably secured to the channels 46 by fasteners (not shown). The inserts 50 are made from a material providing a relatively low coefficient of friction, preferably a lubricated polymer material, to facilitate sliding between the rails 26 and the insert 50. A threaded knob 54 received by each of the channels 46 secures the table 44 to the rails 26.

The table 44 includes a top platform 56 secured to the upstanding legs 48 of the table 44. The upstanding legs 48 of the table 44 are preferably dimensioned to locate the platform 56 at a reduced height compared to the height at which the patient's legs were supported by the stirrups 32 for insertion of the needles into the prostate. The table 44 provides for comfortable support of the patient's legs while keeping them sufficiently raised to prevent sagging of the needles or contact between the inserted needles and the stretcher 12 or the transfer mattress 14.

With the leg support table 44 attached to the rails 26 of the portable patient support 10, the transfer mattress can be inflated, using an air pump connected to the inlet tube 15. The air cushion provided by air escaping from the openings in the bottom sheet of the mattress 14 facilitates sliding movement of the mattress 14 during transfer of the patient from one surface to another, such as from a cart to a CT scanner, for example. The sliding movement provided by the transfer mattress 14 greatly reduces the force needed to transfer the patient and portable device between transport and treatment beds.

As shown in FIG. 3, the portable patient support 10 may also include a protective cover 64 removably secured to the mattress 14 over the stretcher 12. The protective cover 64 may be secured to the mattress 14 by snap attachments carried by the cover 64 and by the tabs connected to the mattress 14.

Figure 5:
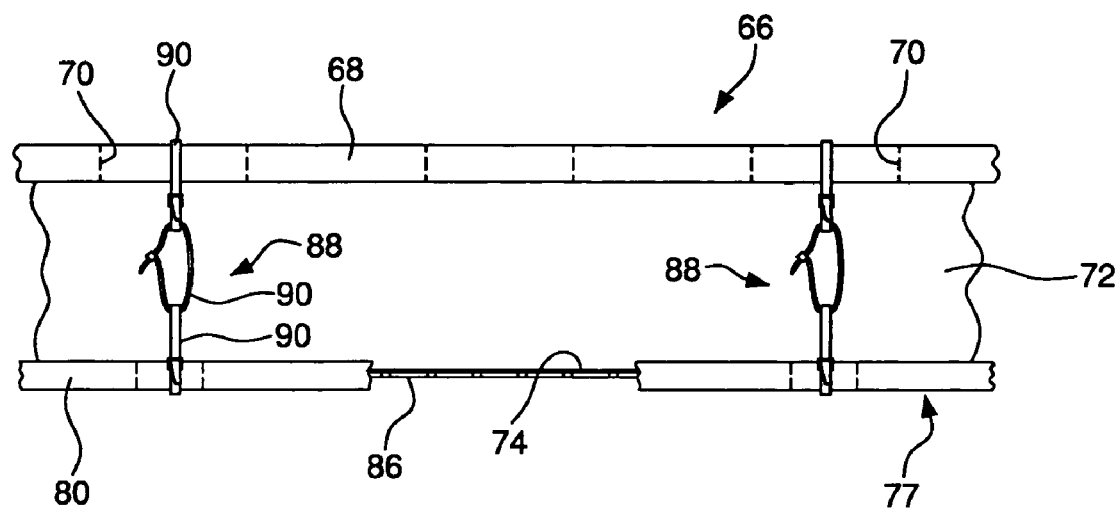
FIG. 5 is a side elevation view of a portable patient support device according to an alternative embodiment of the invention including a lower tray attached to a stretcher such that an inflatable transfer mattress is captured between the tray and the stretcher.
Figure 6:
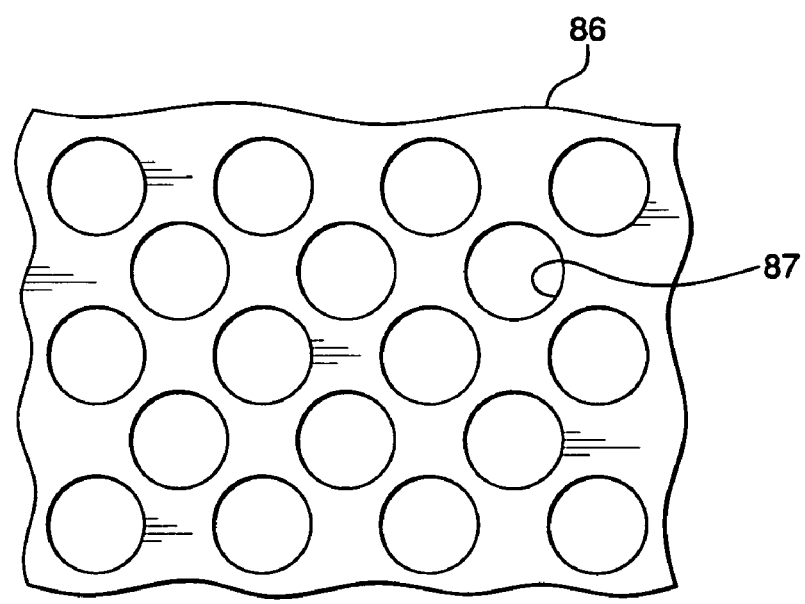
FIG. 6 is a bottom plan view of a perforated plate of the lower tray of FIG. 5.

FIGS. 5 and 6 show a portable patient support device 66 according to another embodiment of the invention. The portable patient support device 66 includes a rigid stretcher 68 that, in the same manner as stretcher 12, includes elongated openings 70 along opposite sides. The patient support device 66 preferably includes an accessory-supporting device having an end cap (not shown) similar to that of portable patient support 10. The portable patient support device 66 would be used in the same manner described above for support 10 to perform a procedure such as a brachytherapy procedure.

The portable patient support device 66 includes a transfer mattress 72 having an inflatable plenum. The transfer mattress 72 includes a bottom sheet 74 that, in known manner, includes a pattern of small holes for discharge of air to create an air cushion beneath the transfer mattress 72.

The portable patient support 66 includes a lower tray 77 located under the transfer mattress 72. The lower tray 77 includes a plate 86 secured to a peripheral frame 80. As shown in FIG. 6, the plate 86 is fenestrated with openings 87 that are closely spaced such that a large percentage of the plate is open. This construction provides for load bearing support by the plate 86 while permitting escaping air from the bottom sheet 74 of transfer mattress 72 to pass through the lower tray 77. The plate 86 of lower tray 77 is preferably made from plastic and the peripheral frame 80 from wood. The invention, however, is not limited to these materials.

As shown in 5, the fenestrated plate 86 of the of the lower tray 77 is relatively thin compared to the peripheral frame 80. In this manner the tray 77 defines a shallow pocket or recess in which a portion of the transfer mattress 72 is received.

The lower tray 77 is secured to the stretcher 68 by expandable connectors 88 having multiple looped members, such as releasable ties 90, that are interlinked in the form of a chain. One of the ties 90 of each connector 88 is looped through one of the openings 70 of the stretcher 68 while another is linked through an opening in the frame 80 of lower tray 77, thereby connecting the stretcher 68 to the tray 77. The chain-like construction of the expandable connectors 88 thus permits a limited amount of relative movement between the stretcher 68 and the lower tray 77. This relative movement provides for inflation and deflation of the transfer mattress 72 while the mattress 72 remains captured between the stretcher 68 and tray 77. The expandable connectors 88 are shown including releasable ties forming a chain but any suitable expanding connector could be used. It is conceivable that the expandable connectors could be constructed in the manner of an accordion to expand or collapse vertically as the air plenum of the transfer mattress 72 is inflated and deflated.

The additional support and containment of the transfer mattress 72 provided by the lower tray 77 and expandable connectors 88 serves to stabilize the air transfer mattress 72 when it's plenum is inflated to limit rolling, side-to-side, motion of a supported patient that might otherwise occur.

The air transfer mattress 72 could be varied in construction from that shown in the figures. For example, the plenum of the air transfer mattress 72 could be modified to optimize the fit of the air transfer mattress within the lower tray 77. Also, the size and number of micro-fenestrations provided in the bottom sheet of the transfer mattress could be varied to account for the partial coverage of perforations by the fenestrated plate 86 of the lower tray 77.

The portable patient support devices described above could be varied in construction from that shown and could be adapted for use with other accessories or attachments. The following is a non-limiting list of modifications or attachments:

(1) an impervious sheet with an air vacuum supply (possibly associated with the air blower of the transfer mattress) for removing air adjacent the patient under the impervious sheet to immobilize the patient during a procedure;

(2) an ankle or knee stirrup;
(3) a bench;
(4) an armboard;
(5) an IV or irrigation bag pole;
(6) slide-adjustable or rail piece;
(7) head support extension;
(8) hand grips;
(9) various positioning devices;
(10) jelly pads or cushions of various size and shape;
(11) prone face hole support;
(12) arm protection devices (to limit arm flailing or for CT passthrough);
(13) a vac-lock adapted for attachment to the patient support device;
(14) straps and buckles;
(15) foldable construction to facilitate storage;
(16) tiltable construction for head adjustment;
(17) varying overall thickness of mattress and stretcher or to include larger pontoons and low slung belly for the mattress to promote stability;
(18) retractable cord or winding handles for air blower;
(19) disposable bags at working end of patient support device;
(20) drape poles;
(21) third arm attachment;
(22) tightening sheets to hold vac-lock bags in place;
(23) snaps for drainage bags and sheets at one end of the device;
(24) tube for HDR connector tubes;
(25) smart logo labels, phone numbers etc. on the equipment;
(26) tool holder;
(27) leveling control for head to toe center of gravity weight problems.

The foregoing describes the invention in terms of embodiments preferred by the inventor for which an enabling description was available, notwithstanding that insubstantial modifications of the invention, including those not presently foreseen, may nonetheless represent equivalents thereto.

What is claimed is:

1. A portable patient support comprising:
a substantially rigid platform for supporting a patient;
an accessory support device located adjacent an end of the platform, the accessory support device adapted for releasable receipt of at least one treatment accessory, the accessory support device including an end cap defining an interior cavity receiving an end portion of the platform; and
a patient transfer device located beneath the platform, the patient transfer device adapted to facilitate sliding movement of a supported patient with respect to an underlying support surface.

2. The portable patient support according to claim 1, wherein the accessory support device includes at least one elongated rail attached to a side wall of the end cap for sliding receipt of a treatment accessory.

3. The portable patient support according to claim 2, further comprising at least one accessory clamping mechanism releasably attached to one of the rails, the accessory clamping mechanism adapted for receipt of an elongated support pole of a treatment accessory.

4. The portable patient support according to claim 3, wherein the end cap includes opposite side walls and wherein the accessory support device includes a pair of rails attached to the opposite side walls, and further includes a pair of clamping mechanisms each adapted to receives an elongated support pole of a leg stirrup accessory for supporting a patients legs.

5. The portable patient support according to claim 1, wherein the end cap includes opposite side walls and the accessory support device includes a pair of elongated rails attached to the opposite side walls of the end cap, and wherein the treatment accessory is a leg support table having a top supported by a plurality of legs, the leg support table also including a pair of elongated channel members secured to the legs of the table, each of the channel members slidingly received by one of the rails of the accessory support device.

6. The portable patient support according to claim 1, wherein the patient transfer device includes an inflatable air mattress including a plurality of holes in a bottom surface for creating a cushion of escaping air beneath the mattress to facilitate sliding movement of the portable patient support with respect to an underlying support surface.

7. The portable patient support according to claim 6, wherein the patient transfer device includes at least one strap secured to the inflatable mattress and wherein the platform includes at least one opening adjacent a periphery of the platform for looped receipt of the strap such that platform is secured to the inflatable mattress.

8. The portable patient support according to claim 7, wherein the patient transfer device includes at least one strap engagement member attached to the mattress adjacent the strap, the strap engagement member adapted to receive the strap and maintain the strap in a looped configuration for securing the platform to the inflatable mattress.

9. The portable patient support according to claim 6, further comprising a tray located beneath the inflatable mattress and a plurality of connectors each attached to the platform and to the tray such that the inflatable mattress is captured between the platform and the tray, the tray including a perforated plate to provide for passage of air through the tray from the holes in the bottom surface of the inflatable mattress.

10. The portable patient support according to claim 9, wherein the connectors are expandable for maintaining attachment between the platform and the tray when the inflatable mattress is in either of a deflated condition and an inflated condition.

11. The portable patient support according to claim 10, wherein each connector includes a plurality of looped elements interlinked in the form of a chain.

12. A portable patient support for performing a brachytherapy procedure comprising:
a substantially rigid platform for supporting a supine patient during a brachytherapy procedure;
an accessory support device including an end cap having opposite side walls and defining an interior cavity in which an end portion of the platform is received, the accessory support device also including a pair of elongated rails secured to the opposite side walls of the end cap;
at least one leg-elevating accessory releasably attached to the elongated rails of the accessory support device for maintaining the legs of a supine patient in an elevated position relative to the platform during a brachytherapy procedure; and
a patient transfer device including an inflatable mattress located beneath the platform, the inflatable mattress including a plurality of holes in a bottom surface of the mattress for creating a cushion of escaping air to facilitate sliding movement of the mattress with respect to an underlying support surface, the patient transfer device including a plurality of straps received by openings in the platform for securing the platform to the mattress.

13. The brachytherapy patient support according to claim 12, wherein the at least one leg-elevating accessory includes a pair of leg stirrups for supporting the legs of a brachytherapy patient in an elevated position sufficient to provide for insertion of brachytherapy needles to the prostate region of the patient.

14. The brachytherapy patient support according to claim 12, wherein the at least one leg-elevating accessory includes a leg support table having a platform for supporting the legs of a brachytherapy patient in an elevated position sufficient to prevent relocation of brachytherapy needles inserted into the prostate region of a brachytherapy patient.

15. A method of performing a brachytherapy procedure comprising the steps of:

providing a portable patient support including a substantially rigid platform and an accessory support device having an end cap including opposite side walls and defining an interior cavity in which an end portion of the platform is received, the accessory support device also including a pair of side rails secured to the opposite side walls of the end cap, the portable patient support further including a patient transfer device having an inflatable mattress located beneath the platform, the inflatable mattress including a plurality of holes in a bottom surface of the mattress for creating a cushion of escaping air to facilitate sliding movement of the mattress with respect to an underlying support surface;

attaching a pair of stirrup accessories to the rails of the accessory support device;

placing the portable patient support on a first treatment support surface at a first location;

placing a brachytherapy patient on the platform of the portable patient support in a substantially supine position with the inflatable mattress in a deflated condition;

placing the legs of the brachytherapy patient in the pair of stirrup accessories such that the legs of the patient are in an elevated position with respect to the platform;

inserting at least one brachytherapy needle into the patient adjacent the patient's prostate;

removing the pair of stirrup accessories from the rails of the accessory support device;

attaching a leg support table to the rails of the accessory support device, the leg support table including a platform for supporting the legs of a brachytherapy patient at a partially elevated position with respect to the elevated position associated with the stirrup accessories;

placing the legs of the brachytherapy patient on the platform of the leg support table at the partially elevated position;

inflating the inflatable mattress of the patient transfer device from the deflated condition to an inflated condition;

transferring the portable patient support from the first treatment support surface to a transport support surface;

transporting the patient to a second location having a second treatment support surface;

transferring the patient from the transport support surface to the second treatment support surface;

deflating the inflatable mattress of the patient transfer device;

introducing a source of radiation into the patient via the at least one needle.

16. The brachytherapy method according to claim 15 further comprising the steps of:

transporting the patient following insertion of the at least one brachytherapy needle and prior to the introduction of the radiation source to a scanning device; and using the scanning device to verify the position of the at least one inserted needle.

17. The brachytherapy method according to claim 16 further comprising the steps of:

creating a computer dosage template based on the verified position of the at least one needle; and inserting the source of radiation via the at least one needle to preselected locations and for preselected dwell times using the computer dosage template.

* * * * *